United States Patent
Xiao et al.

(10) Patent No.: US 10,816,502 B2
(45) Date of Patent: Oct. 27, 2020

(54) USING A BIASED ELECTROCHEMICAL SENSOR FOR ACRYLONITRILE DETECTION

(71) Applicant: HONEYWELL INTERNATIONAL INC., Morris Plains, NJ (US)

(72) Inventors: Lei Xiao, Morris Plains, NJ (US); Qinghui Mu, Morris Plains, NJ (US); Allen Wu, Morris Plains, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 74 days.

(21) Appl. No.: 16/314,424

(22) PCT Filed: Jun. 30, 2016

(86) PCT No.: PCT/CN2016/087893
§ 371 (c)(1),
(2) Date: Dec. 30, 2018

(87) PCT Pub. No.: WO2018/000327
PCT Pub. Date: Jan. 4, 2018

(65) Prior Publication Data
US 2019/0323985 A1    Oct. 24, 2019

(51) Int. Cl.
*G01N 27/407*    (2006.01)
*G01N 27/12*    (2006.01)
*G01N 27/30*    (2006.01)
*G01N 27/404*    (2006.01)
(Continued)

(52) U.S. Cl.
CPC ....... *G01N 27/4076* (2013.01); *G01N 27/126* (2013.01); *G01N 27/301* (2013.01); *G01N 27/4045* (2013.01); *G01N 33/004* (2013.01); *G01N 33/0047* (2013.01); *C07C 255/08* (2013.01)

(58) Field of Classification Search
None
See application file for complete search history.

(56) References Cited

U.S. PATENT DOCUMENTS

| | | | |
|---|---|---|---|
| 4,042,464 | A | 8/1977 | Blurton et al. |
| 4,235,689 | A | 11/1980 | Petersen et al. |
| 4,639,306 | A | 1/1987 | Tomasovic et al. |

(Continued)

FOREIGN PATENT DOCUMENTS

| | | | | |
|---|---|---|---|---|
| CN | 102621205 A | | 8/2012 | |
| CN | 103336041 A | * | 10/2013 | ............. G01N 27/30 |

OTHER PUBLICATIONS

DETCON Operator's Installation and Instruction Manual that covers all Model DM-100 Sensors, Revision 3.3, Jan. 30, 2014 (Year: 2014).*

(Continued)

*Primary Examiner* — Alexander S Noguerola
(74) *Attorney, Agent, or Firm* — Alston & Bird LLP

(57) ABSTRACT

An electrochemical acrylonitrile sensor comprises a housing, an electrolyte disposed within the housing, and a plurality of electrodes in contact with the electrolyte within the housing. The plurality of electrodes comprises a working electrode and a counter electrode. The electrodes comprise a catalytic material, which may comprise gold. A potential is applied between the counter electrode and the working electrode.

4 Claims, 2 Drawing Sheets

(51) Int. Cl.
    *G01N 33/00*     (2006.01)
    *C07C 255/08*     (2006.01)

(56) References Cited

U.S. PATENT DOCUMENTS

| | | |
|---|---|---|
| 4,769,122 A | 9/1988 | Marrese et al. |
| 4,888,295 A | 12/1989 | Zaromb et al. |
| 5,217,112 A | 6/1993 | Almon |
| 5,284,566 A | 2/1994 | Cuomo et al. |
| 2012/0125772 A1 | 5/2012 | Stetter et al. |

OTHER PUBLICATIONS

EPO machine-generated English language translation of Ping et al. CN 103336041 A (Year: 2013).*
EPO computer-generated English language translation of the Description section of CN 102621205 A (Year: 2012).*
International Search Report and Written Opinion for Application No. PCT/CN2016/087893 dated Mar. 6, 2017, 7 pages.
Office Action for Chinese Patent Application No. 201680087282.0, dated Jun. 4, 2020, 18 pages.

\* cited by examiner

USING A BIASED ELECTROCHEMICAL SENSOR FOR ACRYLONITRILE DETECTION

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In monitoring for the presence of various gases, other gases such as carbon monoxide (CO) can be present that can also react within the sensor. For example, the working electrode can comprise a catalyst that can catalyze the reaction of both a target gas and an interferent gas (e.g., such as carbon monoxide). As a result, the presence of the interferent gas may create a cross-sensitivity in the sensor, resulting in the false impression that greater levels of the target gas are present in the ambient gases than are actually present. Due to the danger presented by the presence of various target gases, the threshold level for triggering an alarm can be relatively low, and the cross-sensitivity due to the presence of the interferent may be high enough to create a false alarm for the target gas sensor.

SUMMARY

In an embodiment, an electrochemical acrylonitrile sensor comprises a housing; an electrolyte disposed within the housing; and a plurality of electrodes in contact with the electrolyte within the housing, wherein the plurality of electrodes comprise a working electrode and a counter electrode, wherein a potential is applied between the working electrode and the counter electrode.

In an embodiment, an electrochemical acrylonitrile sensor comprises a housing; an electrolyte disposed within the housing; and a plurality of electrodes in contact with the electrolyte within the housing, wherein the plurality of electrodes comprise: a working electrode, wherein the working electrode comprises a catalytic material, wherein the catalytic material comprises gold; and a counter electrode wherein the counter electrode comprises a catalytic material, wherein the catalytic material comprises gold.

In an embodiment, a method of detecting acrylonitrile, the method comprises receiving an ambient gas into a housing of a acrylonitrile sensor, wherein the ambient gas comprises acrylonitrile and carbon monoxide, and wherein the acrylonitrile sensor comprises a plurality of electrodes in contact with an electrolyte within the housing, wherein the plurality of electrodes comprises a porous working electrode and a counter electrode; applying a voltage potential between the counter electrode and the working electrode; contacting the ambient gas with the porous working electrode; allowing the ambient gas to diffuse through the porous working electrode to contact the electrolyte; generating a current between the porous working electrode and the counter electrode in response to a reaction between the ambient gas and the electrolyte at the surface area of the working electrode; and determining a concentration of the acrylonitrile in the ambient gas based on the current.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
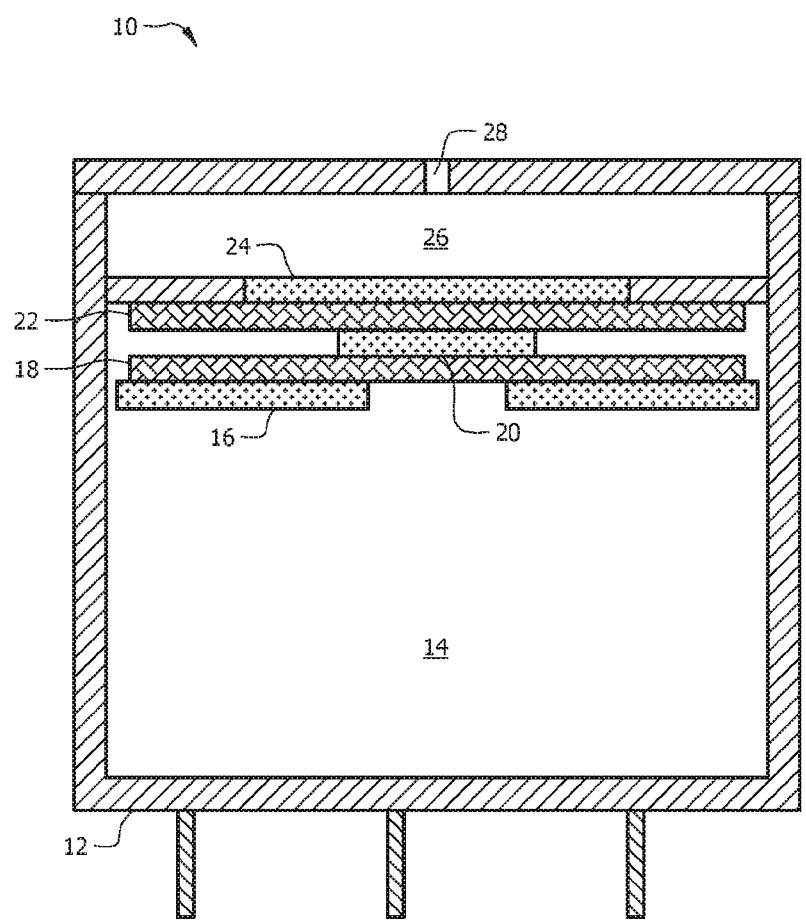
FIG. 1 schematically illustrates a cross section drawing of an electrochemical sensor according to an embodiment.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Due to the extreme toxicity of acrylonitrile gas, various countries have created regulations limiting the exposure of individuals to the gas. As described herein, various sensors have been developed to detect the presence and concentration of acrylonitrile in the atmosphere. Some methods to detect acrylonitrile involve the use of cross sensitivity in ethylene oxide sensors. However, this method may struggle to meet requirements on response time and recovery within the sensor. Also, some sensors may have a high cross sensitivity to carbon monoxide. Due to the high toxicity of acrylonitrile, the sensor alarm level may be typically set to approximately 2 ppm, which means that 1 ppm of CO may trigger a false alarm which makes the instrument unusable in many applications. Accordingly, the removal or reduction of cross-sensitivity to CO in an acrylonitrile sensor may improve safety.

There are a number of ways to enhance the selectivity of electrochemical sensors. First, the selection of the material for the working electrode can affect the overall sensitivity to various chemicals, including a relative sensitivity difference between the target gas and one or more interfering gases. Second, a filter can be used to remove the interfering gas, thereby reducing the cross-sensitivity to the interfering gases. However, the filter typically uses an absorbent or adsorbent that has a limited capacity, thereby limiting the effective life of the sensor. Third, an intermediary electrolyte system can be used. In this system, the selection of the composition of the electrolyte may be carried out so that the electrolyte selectively reacts with the target gases rather than the interfering gases. However, this method can be very complex, and the electrolyte can also have capacity restrictions leading to a limited useful life of the sensor. Fourth, the potential across the electrodes can be selected to remove or reduce the cross sensitivity of the sensor. Further, in some instances the cross sensitivity can be reduced by enlarging the capillary hole. However, this may result in a larger potential being developed in the sensor, which may affect a number of parameters in the sensor design, which may not be suitable for a sensor with a defined sensitivity.

As a novel manner of changing the cross-sensitivity of the electrochemical sensor, the electrochemical gas sensor can comprise a gold catalytic material incorporated into one or more of the electrodes. Additionally, the electrochemical sensor may incorporate an application of a potential across the electrodes. The resulting sensor can have good response to acrylonitrile gas while at the same time having a reduced cross-sensitivity to CO gas. In general, the electrochemical sensor disclosed herein comprises a gas diffusion working electrode, a counter electrode, and optionally, a reference electrode. Each electrode is in contact with an aqueous electrolyte.

FIG. 1 is the cross section drawing of the electrochemical sensor 10. The sensor 10 generally comprises a housing 12 defining a cavity or reservoir 14 designed to hold an electrolyte solution. A working electrode 24 can be placed between an opening 28 and the reservoir 14. A counter electrode 16 and a reference electrode 20 can be positioned within the reservoir. When the gas reacts within the reservoir 14, an electrical current and/or potential can be developed between the electrodes to provide an indication of the concentration of the gas. A reference electrode 20 may also be positioned within the reservoir 14 to provide a reference for the detected current and potential between the working electrode 24 and the counter electrode 16.

The housing 12 defines the interior reservoir 14, and one or more openings 28 can be disposed in the housing to allow a gas to be detected to enter the housing 12 into a gas space 26. The housing 12 can generally be formed from any material that is substantially inert to the electrolyte and gas being measured. In an embodiment, the housing 12 can be formed from a polymeric material, a metal, or a ceramic. For example, the housing can be formed from a material including, but not limited to, acrylonitrile butadiene styrene (ABS), polyphenylene oxide (PPO), polystyrene (PS), polypropylene (PP), polyethylene (PE) (e.g., high density polyethylene (HDPE)), polyphenylene ether (PPE), or any combination or blend thereof.

One or more openings 28 can be formed through the housing 12 to allow the ambient gas to enter the gas space 26 and/or allow any gases generated within the housing to escape. In an embodiment, the electrochemical sensor 10 may comprise at least one inlet opening 28 to allow the ambient gas to enter the housing 12. The opening 28 can be disposed in a cap when a cap is present and/or in a wall of the housing 12. In some embodiments, the opening 28 can comprise a diffusion barrier to restrict the flow of gas (e.g., carbon monoxide, acrylonitrile, etc.) to the working electrode 24. The diffusion barrier can be created by forming the opening 28 as a capillary and/or a film or membrane can be used to control the mass flow rate through the one or more openings 28.

In an embodiment, the opening 28 may serve as a capillary opening to provide a rate limited exchange of the gases between the interior and exterior of the housing 12. In an embodiment, the opening 28 may have a diameter between about 200 µm and about 1.5 mm, where the opening 28 can be formed using a convention drill for larger openings and a laser drill for smaller openings. The opening 28 may have a length between about 0.5 mm and about 5 mm, depending on the thickness of the cap or housing 12. In some embodiments, two or more openings may be present for the inlet gases. When a membrane is used to control the gas flow into and/or out of the housing, the opening diameter may be larger than the sizes listed above as the film can contribute to and/or may be responsible for controlling the flow rate of the gases into and out of the housing 12.

The reservoir comprises the counter electrode 16, the reference electrode 20, and the working electrode 24. In some embodiment, the electrolyte can be contained within the reservoir 14, and the counter electrode 16, the reference electrode 20, and the working electrode 24 can be in electrical contact through the electrolyte. In some embodiments, one or more porous separators 18, 22 or other porous structures can be used to retain the electrolyte in contact with the electrodes. The separators 18, 22 can comprise a porous member that acts as a wick for the retention and transport of the electrolyte between the reservoir and the electrodes while being electrically insulating to prevent shorting due to direct contact between any two electrodes. One or more of the porous separator 18, 22 can extend into the reservoir to provide the electrolyte a path to the electrodes. In an embodiment, a separator 18 can be disposed between the counter electrode 16 and the reference electrode 20, and a separator 22 can be disposed between the reference electrode 20 and the working electrode 24.

One or more of the separators 18, 22 can comprise a nonwoven porous material (e.g., a porous felt member), a woven porous material, a porous polymer (e.g., an open cell foam, a solid porous plastic, etc.), or the like, and is generally chemically inert with respect to the electrolyte and the materials forming the electrodes. In an embodiment, the separator 18, 22 can be formed from various materials that are substantially chemically inert to the electrolyte including, but not limited to, glass (e.g., a glass mat), polymer (plastic discs), ceramics, or the like.

The electrolyte can be any conventional aqueous acidic electrolyte such as sulfuric acid, phosphoric acid, or a neutral ionic solution such as a salt solution (e.g., a lithium salt such as lithium chloride, etc.), or any combination thereof. For example, the electrolyte can comprise sulfuric acid having a molar concentration between about 3 M to about 12 M. Since sulfuric acid is hygroscopic, the concentration can vary from about 10 to about 70 wt % (1 to 11.5 molar) over a relative humidity (RH) range of the environment of about 3 to about 95%. In an embodiment, the electrolyte can comprise phosphoric acid having a concentration in an aqueous solution between about 30% to about 60% $H_3PO_4$ by weight. As another example, the electrolyte can include a lithium chloride salt having about 30% to about 60% LiCl by weight, with the balance being an aqueous solution.

The working electrode 24 may be disposed within the housing 12. The gas entering the sensor 10 can contact one side of the working electrode 24 and pass through working electrode 24 to reach the interface between the working electrode 24 and the electrolyte. The gas can then react to generate the current indicative of the gas concentration. As disclosed herein, the working electrode 24 can comprise a plurality of layers. The base or substrate layer can comprise a hydrophobic material or a hydrophobically treated material. A catalytic material can be formed as an electrode on one side of the working electrode 24 and placed in contact with the electrolyte. In an embodiment, the catalytic material in the working electrode may comprise gold to provide for the detection of acrylonitrile.

In an embodiment, the working electrode 24 can comprise a porous substrate or membrane as the base layer. The substrate can be porous to the gas of interest, which can comprise acrylonitrile. In an embodiment, the substrate can comprise a carbon paper formed of carbon or graphite fibers. In some embodiments, the substrate can be made to be electrically conductive through the addition of a conductive material such as carbon. The use of carbon may provide a sufficient degree of electrical conductivity to allow the current generated by the reaction of the gas with the electrolyte at the surface of the working electrode 24 to be detected by a lead coupled to the working electrode 24. Other electrically conductive substrates may also be used such as carbon felts, porous carbon boards, and/or electrically conductive polymers such as polyacetylene, each of which may be made hydrophobic as described below. Alternatively, an electrically conductive lead can be coupled to the catalytic layer to electrically couple the catalytic material to the external circuitry, as described in more detail herein. In an embodiment, the substrate can be between about 5 mils to about 20 mils thick in some embodiments.

The porous substrate can be hydrophobic to prevent the electrolyte from passing through the working electrode 24. The substrate can be formed from a hydrophobic material, or the substrate can be treated with a hydrophobic material. In an embodiment, the substrate can be made hydrophobic through the impregnation of the substrate with a hydrophobic material such as a fluorinated polymer (e.g., PTFE, etc.). In some embodiments, the substrate or membrane can comprise GEFC-IES (e.g., the copolymer of perfluorosulfonic acid and PTFE, which is commercially available from Golden Energy Fuel Cell Co., Ltd.), Nafion® (a copolymer of polytetrafluoroethylene and perfluoro-3,6-dioxa-4-methyl-7-octene-sulfonic acid, which is commercially available from Dupont™), or pure or nearly pure polytetrafluoroethylene (PTFE). The impregnation process can include disposing a hydrophobic material containing solution or slurry on the substrate using a dipping, coating, or rolling process. Alternatively, a dry composition such as a powder can be applied to the substrate. In some embodiments, an optional sintering process can be used to infuse the hydrophobic material into the substrate to create the hydrophobic base layer for the working electrode 24, where both sides of the hydrophobic base layer are hydrophobic. The sintering process can cause the hydrophobic polymer to bond or fuse with the carbon of the substrate to securely bond the hydrophobic material to the substrate.

The resulting substrates can contain about 30% to about 50% by weight of the hydrophobic polymer. The amount of hydrophobic material added to the substrate can affect the electrical conductivity of the substrate, wherein the electrical conductivity tends to decrease with an increased amount of the hydrophobic material. The amount of the hydrophobic polymer used with the substrate may depend on the degree of hydrophobicity desired, the porosity to the acrylonitrile, and the resulting electrical conductivity of the working electrode.

The catalytic layer can be formed by mixing the desired catalyst with a binder and depositing the mixture on the substrate material. The binder can comprise a solution of perfluorinated ion electrolyte solution (e.g., GEFC-IES, Nafion®, etc.), a hydrophobic material such as PTFE, mixtures thereof, or the like. When used as a binder, the GEFC-IES Nafion®, and/or PTFE can affect the gas diffusion parameters while supporting the electrocatalyst and maximizing the interfaces between catalyst, gas and electrolyte at which the electrochemical processes occur. Glycol or other similar chemicals can be used as a diluent to form a catalyst slurry, recipe or catalyst system, which can be printed on a substrate by a printer.

The catalytic layer might be deposited onto the substrate by for example screen printing, filtering in selected areas from a suspension placed onto the substrate, by spray coating, or any other method suitable for producing a patterned deposition of solid material. Deposition might be of a single material or of more than one material sequentially in layers, so as for example to vary the properties of the electrode material through its thickness or to add a second layer of increased electrical conductivity above or below the layer which is the main site of gas reaction. Once deposited, the printed element can be sintered at an elevated temperature to form the electrode.

In the working electrode 24, the catalytic layer may comprise gold. The catalyst used can be a pure metal powder, a metal powder combined with carbon, or a metal powder supported on an electrically conductive medium such as carbon, or a combination of two or more metal powders either as a blend or as an alloy. The materials used for the individual electrodes can be the same or different.

The counter electrode 16 can be disposed within the housing 12. The counter electrode 16 can comprise a substrate or membrane such as a PTFE membrane, a GEFC-IES membrane, a Nafion® membrane, or the like having a catalytic material disposed thereon. In an embodiment, the catalytic material can be mixed and disposed on the membrane using any suitable process such as rolling, coating, screen printing, or the like to apply the catalytic material on the membrane, as described in more detail herein. The catalyst layer can then be bonded to the membrane through a sintering process as described herein.

In an embodiment, the catalytic material for the counter electrode can comprise one or more metals or metal oxides such as copper, silver, gold, nickel, palladium, platinum, ruthenium, iridium, and/or oxides of these metals. The catalyst loading for the counter electrode 16 can be within any of the ranges described herein for the working electrode 24. In an embodiment, the catalyst loading for the counter electrode 16 can be the same or substantially the same as the catalyst loading for the working electrode 24, the catalyst loading can also be greater than or less than that of the working electrode 24.

In an embodiment, a catalytic material can be added to the working electrode 24 that has a higher catalytic activity towards the target gas such as acrylonitrile than an interfering gas or gases such as carbon monoxide. When the target gas is acrylonitrile and the interfering gas is carbon monoxide, the catalytic material that can be added into the working electrode can comprise gold (Au). In some embodiments, the selection of the catalytic material may provide the desired selectivity. For example, the use of gold as the catalyst (as opposed to, for example, platinum) may allow certain chemical moieties to react without displaying a significant reactivity to others. Thus, the use of gold, along with a bias, may allow for the detection of acrylonitrile with a reduced cross-sensitivity to various gases such as carbon monoxide.

Similarly, the reference electrode 20 can be disposed within the housing 12. The reference electrode 20 can comprise a substrate or membrane such as a PTFE membrane, a GEFC-IES membrane, a Nafion® membrane, or the like having a catalytic material disposed thereon. In an embodiment, the catalytic material can be mixed with a hydrophobic material (e.g., PTFE, etc.) and disposed on the PTFE membrane. Any of the methods used to form the working electrode or the counter electrode can also be used to prepare the reference electrode 20. In an embodiment, the catalytic material used with the reference electrode 20 can comprise one or more metals or metal oxides such as copper, silver, gold, nickel, palladium, platinum, ruthenium, iridium, and/or oxides of these metals. The catalyst loading for the reference electrode 20 can be within any of the ranges described herein for the working electrode 24. In an embodiment, the catalyst loading for the reference electrode 20 can be the same or substantially the same as the catalyst loading for the working electrode 24, the catalyst loading can also be greater than or less than that of the working electrode 24. While illustrated in FIG. 1 as having the reference electrode 20, some embodiments of the electrochemical sensor may not include a reference electrode 20.

In order to detect the current and/or potential difference across the electrodes in response to the presence of the acrylonitrile, one or more leads or electrical contacts can be electrically coupled to the working electrode 24, the reference electrode 20, and/or the counter electrode 16. The lead contacting the working electrode 24 can contact either side of the working electrode 24 since the substrate comprises an electrically conductive material. In order to avoid the corrosive effects of the electrolyte, the lead contacting the working electrode can contact the side of the working electrode 24 that is not in contact with the electrolyte. Leads may be similarly electrically coupled to the counter electrode 16 and the reference electrode 20. The leads can be electrically coupled to external connection pins to provide an electrical connection to external processing circuitry. The external circuitry can detect the current and/or potential difference between the electrodes and convert the current into a corresponding acrylonitrile concentration.

In an embodiment, the sensor 10 may comprise a bias applied to one or more of the electrodes. For example, a potential may be applied between the counter electrode 16 and the working electrode 24. In other words, the sensor 10 may comprise a voltage difference between the counter electrode 16 and the working electrode 24 relative to the reference electrode 20. In an embodiment, the potential (or voltage difference) may be approximately −300 mV.

In use, the sensor 10 can detect an acrylonitrile concentration. In use, the ambient gas can flow into the sensor 10 through the opening 28, which serves as the intake port for the sensor 10. The ambient gas can comprise acrylonitrile. In some embodiments, an interferent gas such as carbon monoxide may also be present. The gas can contact the working electrode and pass through the fine pores of the porous substrate layer to reach the surface of the working electrode 24 treated with the catalyst layer. The electrolyte may be in contact with the surface of the working electrode 24, and the acrylonitrile may react and result in an electrolytic current forming between the working electrode 24 and the counter electrode 16 that corresponds to the concentration of the acrylonitrile in the ambient gas. By measuring the current, the concentration of acrylonitrile can be determined using, for example, the external detection circuitry.

During the measurement process, an interfering gas such as the carbon monoxide can also contact the working electrode 24. The carbon monoxide can react at the surface of the working electrode 24, though the carbon monoxide may not react at the same rate. The carbon monoxide may also experience a diffusional resistance within the sensor 10. The choice of the catalytic material in the working electrode may limit the reactivity of various interferent gases such as carbon monoxide.

In an embodiment in which an additional catalytic material is added to the working electrode 24, the reaction rate of the acrylonitrile at the working electrode 24 can be significantly faster than the reaction of carbon monoxide at the working electrode 24. By adding the catalytic material having a higher reactivity for acrylonitrile than for carbon monoxide, the relative contribution to the overall current from the reaction of the acrylonitrile can be significantly greater than the contribution from the reaction of carbon monoxide, which may reduce the cross-sensitivity of the sensor 10 to carbon monoxide to an acceptable level.

In an embodiment a ratio of: 1) the sensitivity (e.g., as expressed as current per concentration unit such as in units of $\mu$A/ppm, or the like) of the electrochemical sensor to acrylonitrile to 2) the sensitivity (e.g., in units of $\mu$A/ppm, etc.) or cross-sensitivity of the electrochemical sensor to carbon monoxide can be greater than about 20, greater than about 40, greater than about 50, greater than about 60, greater than about 80, greater than about 100, or greater than about 125 using the sensor 10 as described herein. In an embodiment, the ratio of: 1) the sensitivity of the electrochemical sensor to acrylonitrile to the sensitivity of the electrochemical sensor to carbon monoxide can be generally less than about 300, or less than about 200, and the ratio can be in any range from any of the lower end points to any of the upper end points.

Figure 2:
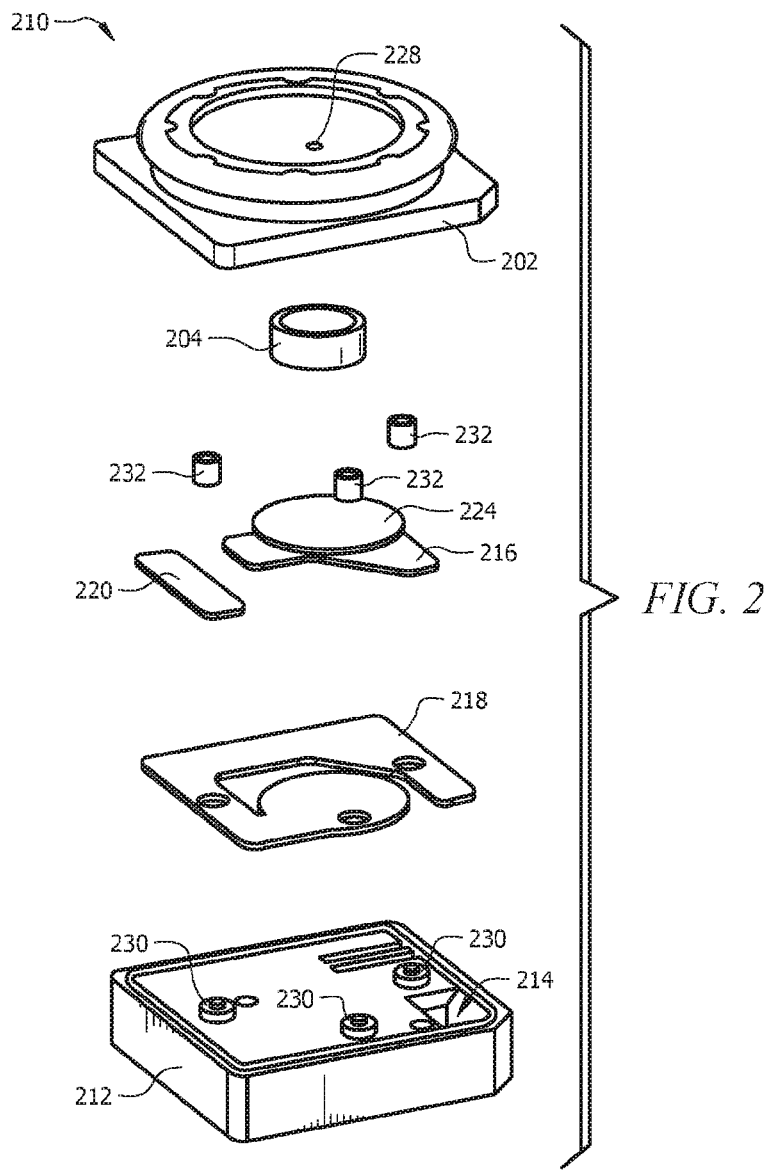
FIG. 2 illustrates an exploded view of an electrochemical sensor according to an embodiment.

Referring to FIG. 2, an embodiment of an electrochemical sensor may comprise a planar arrangement of the electrodes. The sensor 210 may comprise a housing 212 defining a cavity or reservoir 214 designed to hold an electrolyte solution. A working electrode 224 can be placed between an opening 228 and the reservoir 214. A counter electrode 216 and, optionally, a reference electrode 220 can be positioned in a planar arrangement with respect to the working electrode 224, wherein the electrodes may be located in approximately the same plane when the sensor 210 is assembled. When the gas reacts within the reservoir 214, an electrical current and/or potential can be developed between the electrodes to provide an indication of the concentration of the gas. The reference electrode 220 may also be positioned within the sensor 210 to provide a reference for the detected current and potential between the working electrode 224 and the counter electrode 216. In this embodiment, the housing, working electrode 224, counter electrode 216, and the optional reference electrode 220 can be the same or similar to the same component described with respect to FIG. 1, only in a different arrangement or configuration.

The housing 212 defines the interior reservoir 214, and one or more openings 228 can be disposed in the housing to allow a gas to be detected to enter the housing 212. The housing 212 can generally be formed from any material that is substantially inert to the electrolyte and gas being measured. In an embodiment, the housing 212 can be formed from a polymeric material, a metal, or a ceramic. For example, the housing can be formed from a material including, but not limited to, acrylonitrile butadiene styrene (ABS), polyphenylene oxide (PPO), polystyrene (PS), polypropylene (PP), polyethylene (PE) (e.g., high density polyethylene (HDPE)), polyphenylene ether (PPE), or any combination or blend thereof.

In an embodiment, the electrochemical sensor 210 may comprise at least one inlet opening 228 to allow the ambient gas to enter the housing 212. The opening 228 can be disposed in a cap 202 when a cap is present and/or in a wall of the housing 212. In some embodiments, the opening 228 can comprise a diffusion barrier to restrict the flow of gas (e.g., carbon monoxide, acrylonitrile, etc.) to the working electrode 224. The diffusion barrier can be created by forming the opening 228 as a capillary and/or a film or membrane 204 can be used to control the mass flow rate through the one or more openings 228.

In some embodiment, the electrolyte can be contained within the reservoir 214, and the counter electrode 216, the reference electrode 220, and the working electrode 224 can be in electrical contact through the electrolyte. In some embodiments, one or more porous separator 218 or other porous structures can be used to retain the electrolyte in contact with the electrodes. The separator 218 can comprise a porous member that acts as a wick for the retention and transport of the electrolyte between the reservoir 214 and the electrodes while being electrically insulating to prevent shorting due to direct contact between any two electrodes. In an embodiment, a separator 218 may comprise one continuous material operable to contact each of the electrodes. In an embodiment, the separator 218 may be located between the electrodes and the reservoir.

The separators 218 can comprise a nonwoven porous material (e.g., a porous felt member), a woven porous material, a porous polymer (e.g., an open cell foam, a solid porous plastic, etc.), or the like, and is generally chemically inert with respect to the electrolyte and the materials forming the electrodes. In an embodiment, the separator 218 can be formed from various materials that are substantially chemically inert to the electrolyte including, but not limited to, glass (e.g., a glass mat), polymer (plastic discs), ceramics, or the like.

The electrodes 216, 220. 224 may each contact a pin 230 (or electrical contact), wherein the electrodes may be held in contact with the pins 230 with pressure pads 232. In an embodiment of the sensor, the pins 230 may comprise a catalytic material, such as gold. In an embodiment of the sensor 210, a bias may be applied between the working electrode 224 and the counter electrode 216. While illustrated in FIG. 2 as having the reference electrode 220, some embodiments of the electrochemical sensor may not include a reference electrode 220.

In the planar configuration, the sensor can operate in essentially the same manner as described with respect to the stacked configuration of FIG. 1.

Having disclosed various embodiments and methods herein, several embodiments can include, but are not limited to:

In a first embodiment, an electrochemical acrylonitrile sensor comprises a housing, an electrolyte disposed within the housing, and a plurality of electrodes in contact with the electrolyte within the housing, wherein the plurality of electrodes comprise a working electrode and a counter electrode, wherein a potential is applied between the working electrode and the counter electrode.

A second embodiment can include the sensor of the first embodiment, wherein the potential is greater than approximately 300 mV.

A third embodiment can include the sensor of the first or second embodiment, wherein the working electrode comprises a catalytic material.

A fourth embodiment can include the sensor of the third embodiment, wherein the catalytic material comprises gold (Au).

A fifth embodiment can include the sensor of any of the first to fourth embodiments, wherein the counter electrode comprises a catalytic material.

A sixth embodiment can include the sensor of the fifth embodiment, wherein the catalytic material comprises gold (Au).

A seventh embodiment can include the sensor of any of the first to sixth embodiments, wherein the sensor is configured to detect acrylonitrile, and wherein a ratio of 1) a sensitivity of the sensor to acrylonitrile to 2) a sensitivity of the sensor to carbon monoxide is greater than about 50.

An eighth embodiment can include the sensor of any of the first to seventh embodiments, wherein the electrodes comprise a planar arrangement.

An ninth embodiment can include the sensor of any of the first to seventh embodiments, wherein the electrodes comprise a stacked arrangement.

In an tenth embodiment, an electrochemical acrylonitrile sensor comprises a housing; an electrolyte disposed within the housing; and a plurality of electrodes in contact with the electrolyte within the housing, wherein the plurality of electrodes comprise: a working electrode, wherein the working electrode comprises a catalytic material, wherein the catalytic material comprises gold; and a counter electrode wherein the counter electrode comprises a catalytic material, wherein the catalytic material comprises gold.

An eleventh embodiment can include the sensor of the tenth embodiment, wherein a potential is applied between the working electrode and the counter electrode.

A twelfth embodiment can include the sensor of the eleventh embodiment, wherein the potential is approximately 300 mV.

A thirteenth embodiment can include the sensor of any of the tenth to twelfth embodiments, wherein the sensor is configured to detect acrylonitrile, and wherein a ratio of 1) a sensitivity of the sensor to acrylonitrile to 2) a sensitivity of the sensor to carbon monoxide is greater than about 50.

A fourteenth embodiment can include the sensor of any of the tenth to thirteenth embodiments, further comprising a reference electrode.

A fifteenth embodiment can include the sensor of the fourteenth embodiment, further comprising a voltage difference between the working electrode and the counter electrode relative to the reference electrode.

A sixteenth embodiment can include the sensor of the fifteenth embodiment, wherein the voltage difference is approximately 300 mV.

In a seventeenth embodiment, a method of detecting acrylonitrile, the method comprises receiving an ambient gas into a housing of a acrylonitrile sensor, wherein the ambient gas comprises acrylonitrile and carbon monoxide, and wherein the acrylonitrile sensor comprises a plurality of electrodes in contact with an electrolyte within the housing, wherein the plurality of electrodes comprises a porous working electrode and a counter electrode; applying a voltage potential between the counter electrode and the working electrode; contacting the ambient gas with the porous working electrode; allowing the ambient gas to diffuse through the porous working electrode to contact the electrolyte; generating a current between the porous working electrode and the counter electrode in response to a reaction between the ambient gas and the electrolyte at the surface area of the working electrode; and determining a concentration of the acrylonitrile in the ambient gas based on the current.

An eighteenth embodiment can include the method of the seventeenth embodiment, wherein a ratio of 1) a sensitivity of the sensor to acrylonitrile to 2) a sensitivity of the sensor to carbon monoxide is greater than about 20.

A nineteenth embodiment can include the method of the seventeenth or eighteenth embodiment, wherein the working electrode comprises a catalytic gold material.

A twentieth embodiment can include the method of any of the seventeenth to nineteenth embodiments, wherein the counter electrode comprises a catalytic gold material.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises", "includes", and "having" should be understood to provide support for narrower terms such as "consisting of", "consisting essentially of", and "comprised substantially of". Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method of detecting acrylonitrile, the method comprising:
   receiving an ambient gas into a housing of an acrylonitrile sensor, wherein the ambient gas comprises acrylonitrile and carbon monoxide, and wherein the acrylonitrile sensor comprises a plurality of electrodes in contact with an electrolyte within the housing, wherein the plurality of electrodes comprises a porous working electrode and a counter electrode;
   applying a voltage potential between the counter electrode and the porous working electrode;
   contacting the ambient gas with the porous working electrode;
   allowing the ambient gas to diffuse through the porous working electrode to contact the electrolyte;
   generating a current between the porous working electrode and the counter electrode in response to a reaction between the ambient gas and the electrolyte at a surface area of the porous working electrode; and
   determining a concentration of the acrylonitrile in the ambient gas based on the current.

2. The method of claim 1, wherein a ratio of 1) a sensitivity of the sensor to acrylonitrile to 2) a sensitivity of the sensor to carbon monoxide is greater than about 20.

3. The method of claim 1 wherein the working electrode comprises a catalytic gold material.

4. The method of claim 1, wherein the counter electrode comprises a catalytic gold material.

* * * * *